United States Patent [19]

Houghton et al.

[11] Patent Number: 4,991,432

[45] Date of Patent: Feb. 12, 1991

[54] SENSOR AND SYSTEM FOR CONTINUOUS DETERMINATION OF SHEET CHARACTERISTICS

[75] Inventors: Paul J. Houghton; Lee M. Chase, both of Los Gatos; John D. Goss, San Jose; Kent M. Norton, Los Gatos, all of Calif.

[73] Assignee: Measurex, Cupertino, Calif.

[21] Appl. No.: 388,567

[22] Filed: Aug. 1, 1989

Related U.S. Application Data

[63] Continuation of Ser. No. 56,332, May 26, 1987, Pat. No. 4,864,851, which is a continuation of Ser. No. 784,213, Oct. 4, 1985, abandoned, and a continuation-in-part of Ser. No. 730,406, May 2, 1985, abandoned.

[51] Int. Cl.$^5$ ............................................. G01L 5/04
[52] U.S. Cl. ........................................ 73/159; 73/852
[58] Field of Search ...................... 73/159, 849, 852; 162/263, 49

[56] References Cited

U.S. PATENT DOCUMENTS

| | | | |
|---|---|---|---|
| 3,158,021 | 11/1964 | Walters et al. | 73/159 |
| 3,677,076 | 7/1972 | Herzhoff et al. | 73/159 |
| 3,718,037 | 2/1973 | Stringer et al. | 73/159 |
| 4,313,348 | 2/1982 | Madsen | 73/852 |
| 4,864,851 | 9/1989 | Haughton | 73/159 |

Primary Examiner—Robert Raevis
Attorney, Agent, or Firm—Spensley Horn Jubas & Lubitz

[57] ABSTRACT

A sensor for sensing a quality of a sheet, such as a paper sheet, related to elastic modulus and bending stiffness as it is being made including a sheet support in the form of a ring and a free running wheel, which depresses the paper into the center of the ring as the paper passes over it. A force transducer mounted to the wheel senses the force of the deflected paper on the wheel and provides a measure of a characteristic of the paper related to its elastic modulus and being stiffness. Alternatively, or in addition, a displacement sensor may be used to sense the distance that the sheet is displaced by the wheel into the ring. These factors, together with basis weight, thickness and paper velocity may be used to determine the strength of the paper on a continuous basis.

21 Claims, 3 Drawing Sheets

SENSOR AND SYSTEM FOR CONTINUOUS DETERMINATION OF SHEET CHARACTERISTICS

This is a continuation of copending U.S. patent application Ser. No. 07/056,332, filed May 26, 1987 (now U.S. Pat. No. 4,864,851), which in turn is a continuation of copending U.S. patent application Ser. No. 06/784,213, filed Oct. 4, 1985, now abandoned. U.S patent application Ser. No. 07/056,332 is also a continuation-in-part of copending U.S. patent application Ser. No. 06/730,406, filed May 2, 1985, now abandoned.

BACKGROUND OF THE INVENTION

One of the critical parameters involved in the manufacture of paper is its strength. Virtually all paper manufactured is sold with a strength specification of some sort, but up to the present time it has not been practical to accurately measure the strength of paper "on line" as it is being manufactured. Since paper making is a high speed continuous process, large amounts of paper can easily be produced before the strength of the paper made can be confirmed by subsequent measurement.

Strength specifications for paper are usually given in terms of an empirical destructive test, one of the more common of these being the "burst pressure" or "Mullen" test. A burst pressure test is conducted by clamping a sample of the paper between two circular clamping rings having a specified standard inside diameter, and building up pressure on one side of the paper until the paper bursts (using a rubber diaphragm and liquid pressure). The pressure required to burst the paper is known as the "burst pressure" and is the figure often used to specify the required strength.

Needless to say, the burst pressure test does not lend itself for use in connection with the continuous measurement of paper strength. Because of its widespread popularity, however, any other method used to measure the strength of paper should provide results which correlate with the standard burst pressure test.

SUMMARY OF THE INVENTION

Accordingly, it is an object of the present invention to provide an "on-line" continuous measurement of paper strength. By its nature, a measurement of strength is destructive. Fortunately, however, the strength of paper has been found to be related to factors which are known, or can be measured on a continuous basis. The factors which have been identified as affecting the strength are the "elastic modulus" of the paper, its basis weight and its thickness. Quotation marks are used around the term "elastic modulus" to indicate that the function, while related to the elastic modulus is really an empirically derived factor which depends on other characteristics also. The most important secondary factor involved is the bending stiffness of the sheet. In any particular paper making set up, changing the speed of the web also affects the strength of the resulting product.

Elastic modulus and bending stiffness are difficult, if not impossible to measure directly on a moving web of paper. However, a sensor has been developed which senses a physical manifestation of the paper related to these characteristics and provides an output which, when taken together with the other aforementioned factors, can be used to determine paper strength. An empirical equation relating these factors with strength has been developed.

A clear understanding of the invention can be had by referring to the following detailed description of the presently preferred embodiment of the invention together with the appended drawings.

DETAILED DESCRIPTION OF THE INVENTION

Paper is ordinarily made in a continuous sheet by high speed machines, often several hundred feet in length. The process involves laying a wet mass of wood pulp onto a moving wire fabric belt, drying the mass, and finally calendering the sheet to give it the desired surface finish. The present invention is most advantageously used to monitor the strength of the paper after the final calendering operation, and before the paper is rolled up on the final reel. The reroll motor (not shown) maintains a constant tension in the sheet between the calender and the reroll reel. Since the strength of the paper produced may vary across the sheet as well as along the sheet, the present invention preferably involves the use of a scanning system whereby the sensors scan across the width of the paper while the paper is being fed out the calender and into the reroll system.

Figure 1:
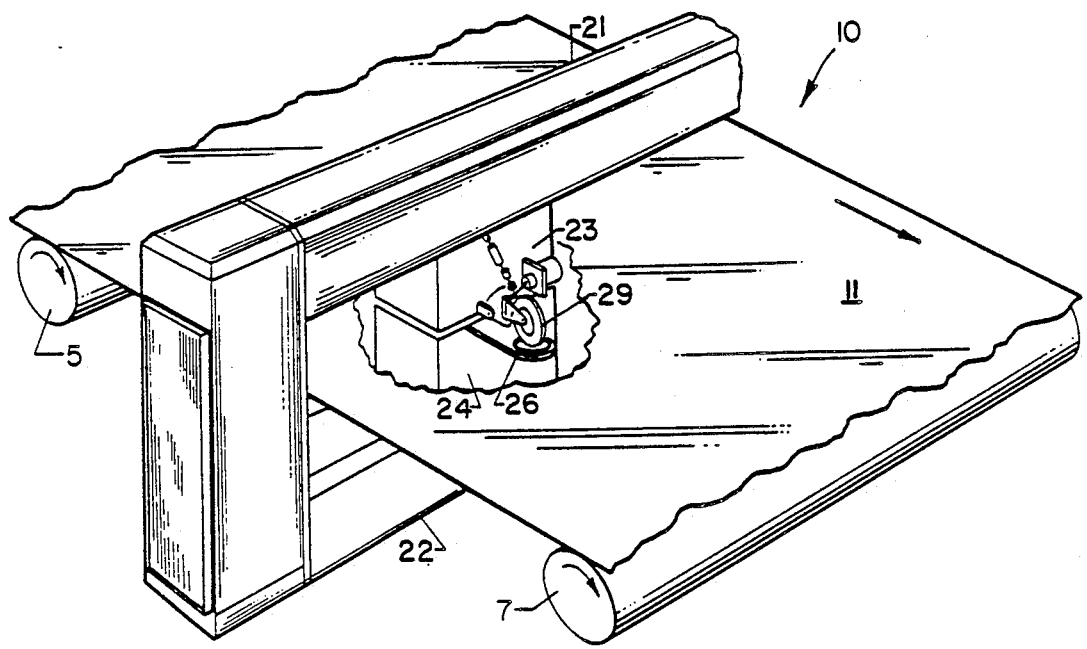
FIG. 1 is a perspective view of the sensing portion of the invented apparatus as installed in a paper making machine.
Figure 6:
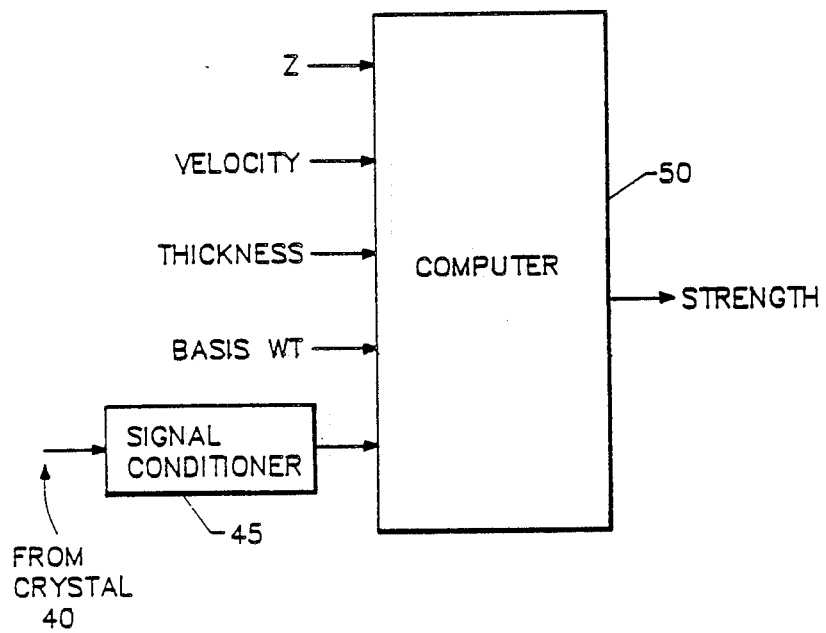
FIG. 6 is a block diagram of the electronic portion of the invention.

FIG. 1 shows a scanning station 10 which, as noted above, is preferably located after the final calender rolls. A web of paper 11, which is driven by rotation of rolls 5, 7, can be seen passing through the scanning station between two transverse beams 21 and 22 on which are mounted upper and lower gage support members 23 and 24. The web paper 11 in FIG. 1 is shown with cut out area so that the relationship between the gage support members can be seen. A motor within the scanning station is coupled to, and drives the gage support members 23, 24 back and forth across the width of the paper in a continuous scanning motion, keeping them in alignment at all times.

The gage support members carry four sets of sensors which provide the data used to calculate paper strength. The four factors used are basis weight, thickness, "elastic modulus", and the velocity of the web. Means for determining basis weight, thickness, and paper velocity are all known in the prior art and are therefore not shown or discussed herein. Thickness and paper velocity are relatively simple to measure, and many methods are known in the prior art. Basis weight is a more complex matter, but a suitable method is disclosed in Bossen et al U.S. Pat. No. 3,757,122. The fourth sensor provides data which relates to the "elastic modulus" of the paper. As noted above, the sensor is responsive not only to the elastic modulus of the sheet, but also to its stiffness in bending.

Figure 2:
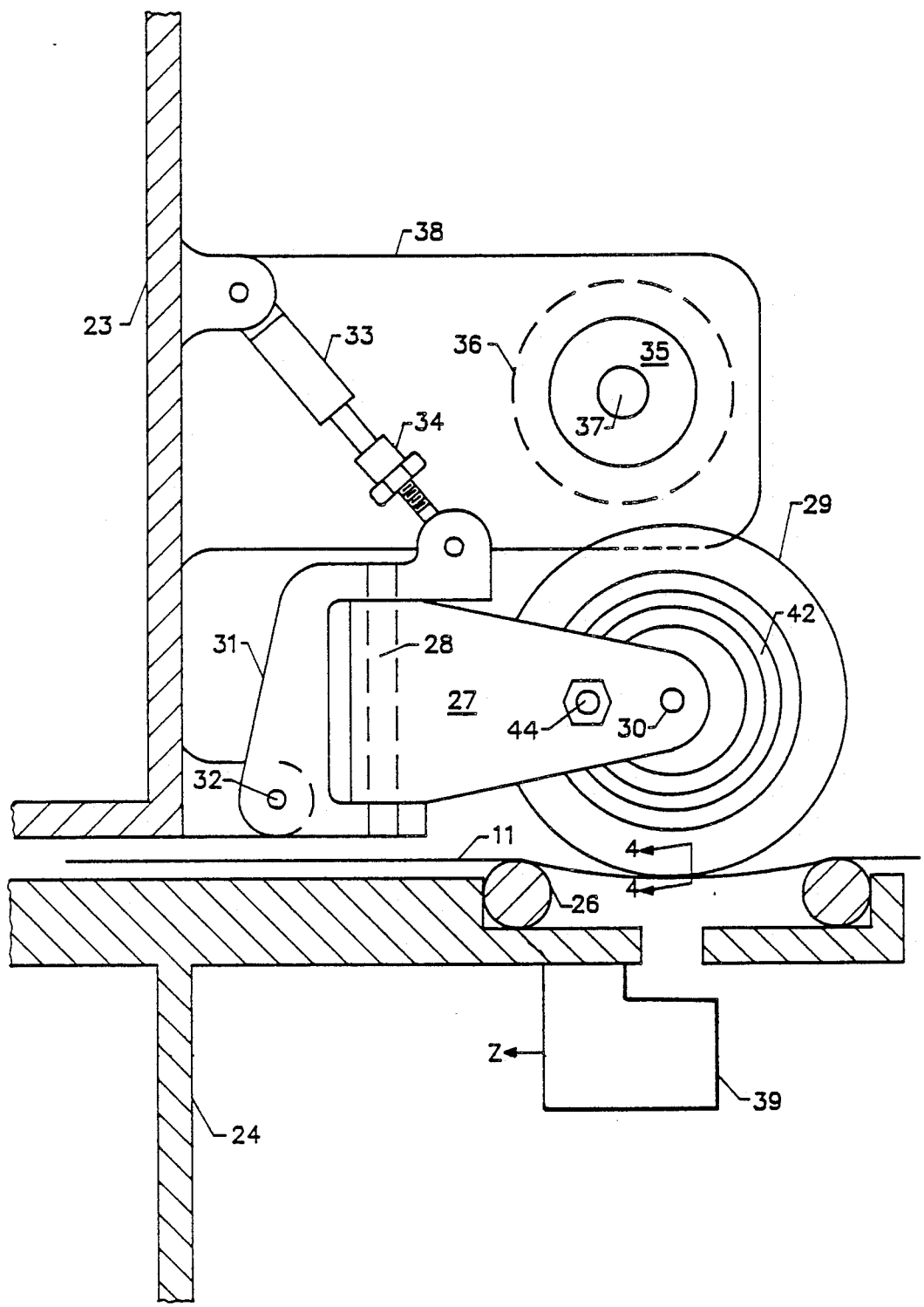
FIG. 2 is a partly cross sectional side view of the sensor for sensing the "elastic modulus" of the paper.

FIG. 2 shows a partially sectioned side view of the invented "elastic modulus" sensor Lower gage support 24 supports a horizontal ring 26 whose top surface is preferably aligned with the paper web 11. While a ring such as ring 26 is the preferred method of support, other forms of supporting structure could be used which support the paper in the vicinity of a central region.

Upper gage support 23 carries the sensing wheel assembly which comprises bracket 31, yoke 27 and wheel 29. Pins 28 and 32 allow the wheel freedom to move both horizontally and also up and down while bearings on axle 30 (not shown) permit the wheel to rotate freely. Up and down motion of the wheel 29 is controlled by air cylinder 33. In its extended position, air cylinder 33 positions the lower portion of the periphery of wheel 29 a fixed distance below the top surface of ring 26. For purposes of example, and not by way of limitation, if the diameters of wheel 29 and ring 26 are each about 5 inches, a satisfactory position for the lowest point on wheel 29 may be ¼ inch below the top surface of ring 26. When the air cylinder 33 is retracted, wheel 29 will be in contact with rubber covered wheel 35. Stop 34 adjusts the upper position of wheel 29 so as to set the force exerted by the rubber on wheel 29. The purpose of this arrangement will be discussed below.

Inset in wheel 29 are a piezoelectric dynamic force transducer 40 and contact button 41. The outer surface of contact button 41 conforms to the surface of the wheel 29. A force on contact button 41 will compress the piezoelectric transducer 40 so as to generate a voltage between its faces. This voltage is conducted by a pair of wires to slip rings 42 and 43 and thence through a pair of brushes 44 (only one of which can be seen in the drawings) to signal conditioner 45.

Figure 5:
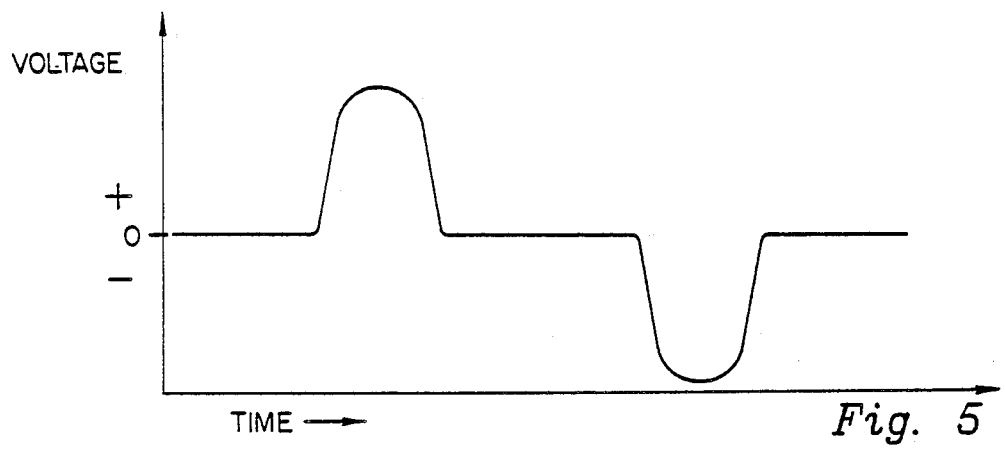
FIG. 5 shows the waveform of the signal produced by the sensor of FIG. 2.

Each time button 41 contacts the paper web, a pair of voltage pulses are generated as shown in FIG. 5. The positive pulse generated when the button contacts the paper is used to trigger a gate in the signal conditioner 45 so that the signal conditioning circuitry will be in a condition to accept the negative pulse which follows. The purpose of gating the negative pulse is to reduce the effect of any electrical noise in the system. The negative pulse is integrated in signal conditioner 45, as is common practice with piezoelectric transducer signals. Since the voltage output of a piezoelectric crystal is proportional to the rate of change of the force applied between its faces, the magnitude of the integrated negative pulse is proportional to the force of the paper web on the contact button.

Figure 4:
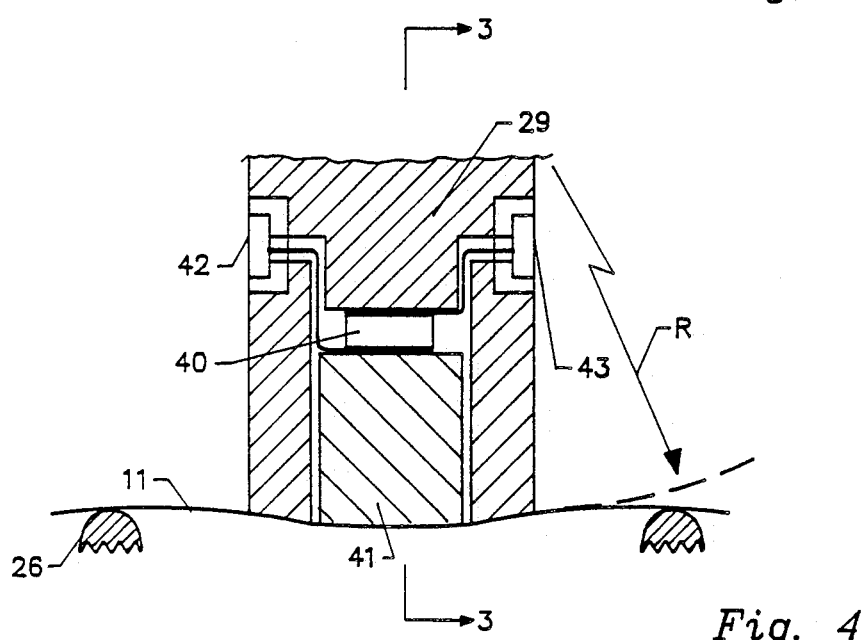
FIG. 4 is a fragmentary cross sectional view of the sensing wheel of FIG. 2 taken at 4—4 of FIG. 2.
Figure 3:
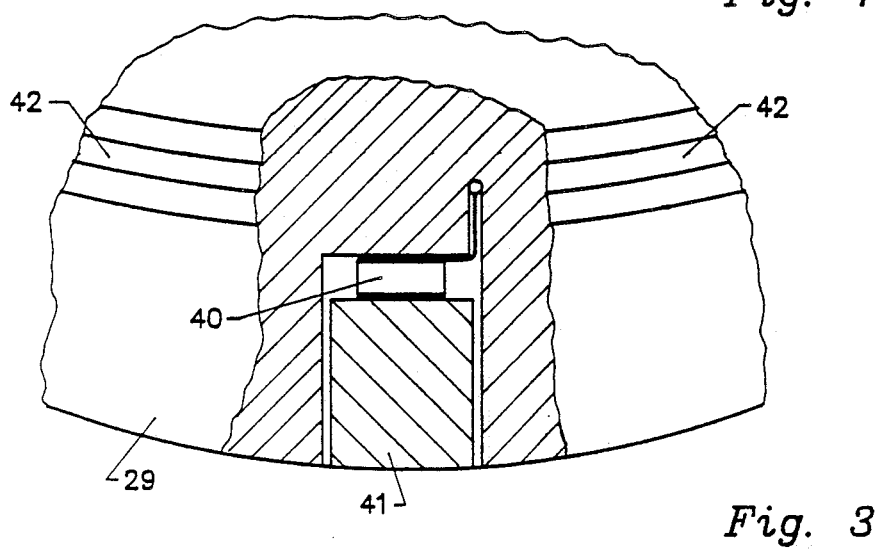
FIG. 3 is a partial side view, partly cross sectioned, of the sensing wheel of the sensor of FIG. 2.

The periphery of wheel 29 is not cylindrical but, rather, is perferably approximately spherical. That is, the radius R as shown in FIG. 4 is preferably approximately equal to one half the wheel diameter. The wheel surface need not be spherical, but is preferably at least convex, particularly if a load sensor is utilized in the preferred embodiment disclosed herein is used. The force exerted by the paper on the wheel is a function of several factors including the tension on the sheet, the elastic modulus of the paper, the bending stiffness of the paper, and the physical dimensions of the gaging components.

The output of signal conditioner 45 (the integrated negative voltage pulse from piezoelectric crystal 40) is coupled to computer 50 where it is combined with signals from the other sensors to arrive at a value for the strength of the paper. An empirical equation has been developed which provides a strength determination which correlates well with the standard "Mullen" test. This equation is:

$$S = A \times \frac{L}{Lav} + (B \times W^E \times T^F) - C \times V^D \qquad (1)$$

where

S is the strength of the paper,
A,B,C,D,E and F are constants,
L is the force of the paper on button 41 (the integrated negative pulse output of crystal 40),
Lav is the average value of L over the width of the paper,
W basis weight of the paper,
T is the thickness of the paper, and
V is the velocity of the paper web leaving the calender.

The above equation has been found to be applicable to a wide variety of papers being manufactured. The constants A, B, C, D, E and F vary somewhat depending on the particular paper being made, but generally fall within the following ranges (where basis weight is in pounds per 1000 square feet, thickness is in mils, and velocity is in feet per minute):

A from 20 to 22
B from 0.5 to 5
C from 0 to 0.07
D from 0.5 to 5
E from 1 to 2
F from −1 to +1

The following table lists several specific cases by way of example. The samples listed are all kraft paper to various grades.

| SAMPLE NO. | S (#/IN²) | W (#/MFT²) | T (MILS) | V (FT/MIN) | A | B | C | D | E | F |
|---|---|---|---|---|---|---|---|---|---|---|
| 1 | 83.58 | 32.5 | 10.9 | 1630 | 21 | 1.03 | $8.4 \times 10^{-7}$ | 2.30 | 1.57 | −.45 |
| 2 | 60.50 | 26.0 | 8.4 | 2095 | 21 | 1.03 | $7.0 \times 10^{-1}$ | .476 | 1.57 | −.45 |
| 3 | 54.75 | 22.8 | 8.3 | 2300 | 21 | 1.03 | $1.42 \times 10^{-16}$ | 5.10 | 1.57 | −.45 |
| 4 | 43.80 | 19.7 | 6.7 | 1849 | 21 | 1.03 | $1.23 \times 10^{-12}$ | 4.07 | 1.57 | −.45 |

In all of the above cases, the tension on the sheet was kept at a constant value of 60 pounds per lineal inch of width of the paper. Lav for the various samples (in arbitrary units) varied from about 3 to 4.5, and the variation in L across the width of the sheet was in all cases of the order of +20%. As can be seen, the factor $CV^D$ in some cases can be relatively small compared to the other factors in the equation, and in those cases could be neglected or replaced with a constant with relatively small loss in accuracy. It also may be noted that the force on the wheel 29 appears only as L/Lav. This indicates that the "elastic modulus" is primarily an indicator of how the paper strength varies across the width of the paper, while the average strength is primarily determined as a function of basis weight and thickness.

The above data presupposes that the lowest point on the periphery of wheel 29 is maintained at a constant distance below the top surface of ring 26. If the mechanical rigidity of the structure is such that the spacing cannot be maintained, sensing means can easily be adapted to sense the relative positions of wheel 29 and ring 26, and to apply a correction to the L/Lav term to account for variations. A conventional sensor for this purpose is shown diagramatically in FIG. 2 identified by the numeral 39. The output of displacement sensor 39 is designated as "Z" and is used to modify the L/Lav term of equation (1) as a multiplier, viz. $f(Z) \times L/Lav$.

It has been found desirable to standardize the output of signal conditioner 45 from time to time. By retracting air cylinder 33 until stop 34 rests against the cylinder, wheel 29 is raised out of contact with the paper web and into contact with wheel 35. Wheel 35 is made of a rubberlike material and is driven with a surface speed approximately that of web 11 by motor 36 through shaft 37. The hardness of wheel 35 is selected so that the force on crystal 40 will be in the range experienced by the crystal when it is bearing against a paper web. By running the sensor in the standardizing position, the output of the "elastic modulus" sensor can be standardized, and the whole system set up without running the paper making machine.

What has been described is a novel sensor and system for determining paper strength "on line". A presently preferred embodiment has been disclosed for purposes of illustration, but it will be understood that persons skilled in the art will be able to make changes thereto within the spirit of the invention and therefore the scope of the invention should be limited only by the following claims.

We claim:

1. A sensor for non-destructively and continuously determining a physical characteristic of a continuous moving sheet under tension, the sensor comprising:
   a sheet support having a sheet supporting surface adapted to support the moving sheet at a plurality of locations defining an open area therebetween, wherein one of the locations is adjacent to the open area in a direction perpendicular to the direction of motion of the sheet and a second location is disposed on the side of the open area opposite the one location;
   a sheet displacing member adapted to be disposed at least partially within the open area, the member having a sheet displacing surface adapted to non-destructively displace a portion of the moving sheet into the open area; and
   a displacement sensing means operatively coupled to the sheet support and the member to sense the distance the sheet displacing member displaces the sheet into the open area, and to generate signals indicative of the sensed distance.

2. The sensor of claim 1, further comprising a computer operatively coupled to the displacement sensing means to receive the signals and compute a physical characteristic of the sheet based upon the signals.

3. The sensor of claim 2, wherein the physical characteristic is sheet failure strength.

4. The sensor of claim 1, wherein the sheet support is further adapted to support the moving sheet at a third location adjacent to the open area in the direction of motion of the sheet and at a fourth location disposed on the side of the open area opposite the third location.

5. The sensor of claim 4, wherein the sheet support includes a ring having a substantially circular sheet supporting surface adapted to support the moving sheet at the four locations.

6. A system for non-destructively and continuously determining a physical characteristic of a continuous moving sheet
   having first and second opposing major surfaces and being under tension in the direction of motion, the system comprising:
   a sheet support having at least one sheet supporting surface supporting the first side of the moving sheet at a plurality of locations defining an open area therebetween, wherein a first of the locations is adjacent to the open area in a direction perpendicular to the direction of motion of the sheet and a second of the locations is disposed on the side of the open area opposite the first location;
   a sheet displacing member disposed at least partially within the open area and pressing the second side of the sheet into the open area, the member having a sheet displacing surface adapted to non-destructively displace a portion of the moving sheet into the open area; and
   a displacement sensor operative to sense the displacement of the sheet into the open area, and to continuously generate signals indicative of the amount of the sensed displacement.

7. The system of claim 6, further comprising a computer operatively coupled to the displacement sensor to receive the signals and compute a physical characteristic of the sheet based upon the signals.

8. The system of claim 7, wherein the physical characteristic is sheet failure strength.

9. A method for non-destructively and continuously determining a physical characteristic of a continuous moving sheet under tension, comprising the steps of:
   non-destructively supporting one side of the moving sheet at least at two locations, wherein the at least two locations are spaced from each other in a direction perpendicular to the direction of sheet motion and define an open area therebetween;
   non-destructively forcing a sheet displacing member against the opposite side of the sheet such that the sheet displacing the member is displaced at least partially within the open area; and
   continuously sensing the distance the moving sheet is displaced into the open area.

10. The method of claim 9, further comprising the step of determining a physical characteristic of the sheet based upon the sensed distance.

11. The method of claim 10, wherein the physical characteristic is sheet failure strength.

12. The method of claim 9, further comprising the steps of supporting the sheet against the force of the displacing member at third and fourth locations adjacent the open area, wherein the third location is adjacent to the open area in the direction of sheet motion and the fourth location is on the side of the open area opposite the third location.

13. The method of claim 9, wherein the sheet is supported at a plurality of locations defining a circular open area.

14. A sensor for non-destructively and continuously determining a physical characteristic of a continuous moving sheet under tension, comprising:
   support means for supporting one side of the moving sheet at least at two locations adjacent to an open area defined therebetween, wherein one of the locations is adjacent to the open area in a direction perpendicular to the direction of motion of the sheet and a second location is disposed on the side of the open space opposite the one location;

displacement means for non-destructively pressing against the sheet over an area less than the entire open area for displacing the sheet into the open area; and sensor means, operatively coupled to the support means and to the displacement means, for continuously sensing the distance that the displacement means displaces the sheet into the open area.

15. The sensor of claim 14, wherein the support means is a ring defining a substantially circular open area.

16. The sensor of claim 14, wherein the displacement means is a freely rotating wheel.

17. The sensor of claim 14, further comprising computing means operatively coupled to the sensor means for determining a physical characteristic of the sheet based upon the sensed distance.

18. The sensor of claim 17, wherein the computing means is operative to compute a physical characteristic of a paper sheet based upon the sensed distance.

19. An on-line sensor for non-destructively determining a physical characteristic of a continuous, moving sheet under tension in the direction of motion, the sensor comprising:

a sheet support having a surface for supporting said moving sheet at a plurality of locations defining a region having an area substantially smaller than that of the moving sheet;

a sheet displacing member adapted to be disposed at least partially within the defined region, the member having a surface adapted to non-destructively displace a portion of the moving sheet into the region; and displacement sensing means operatively associated with the member for sensing the displacement of the sheet into the region and continuously generating signals indicative of the sensed displacement.

20. An on-line sensor for non-destructively and continuously determining a physical characteristic of a continuous, traveling paper sheet under tension in the direction of motion, said characteristic being usable to determine the failure strength of the paper sheet, the sensor comprising:

a ring having a substantially circular sheet supporting surface and defining a central region within the confines of the supporting surface;

a sheet displacing member adapted to non-destructively displace a portion of the paper sheet at least partially within the central region of the ring; and displacement sensing means operatively associated with the sheet displacing member for sensing the displacement of the sheet and continuously generating signals indicative of the displacement.

21. The sensor of claim 20, in which the sheet displacing member includes an idler wheel having an outer surface adapted to engage the paper sheet.

* * * * *